US008626314B2

(12) United States Patent
Swoyer et al.

(10) Patent No.: US 8,626,314 B2
(45) Date of Patent: Jan. 7, 2014

(54) IMPLANTABLE MEDICAL LEAD INCLUDING A PLURALITY OF TINE ELEMENTS

(75) Inventors: John M. Swoyer, Andover, MN (US); Keith R. Carlton, Minneapolis, MN (US); Martin T. Gerber, Maple Grove, MN (US); George J. Mamo, Ellicott City, MD (US); Michele Spinelli, Milan (IT); Steven D. Hartle, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/183,289

(22) Filed: Jul. 14, 2011

(65) Prior Publication Data

US 2011/0270269 A1 Nov. 3, 2011

Related U.S. Application Data

(63) Continuation of application No. 11/589,407, filed on Oct. 30, 2006, now Pat. No. 8,000,805, which is a continuation of application No. 11/352,552, filed on Feb. 13, 2006, now Pat. No. 8,036,756, which is a continuation of application No. 10/004,732, filed on Nov. 9, 2001, now Pat. No. 6,999,819.

(60) Provisional application No. 60/316,582, filed on Aug. 31, 2001.

(51) Int. Cl.
*A61N 1/05* (2006.01)
(52) U.S. Cl.
USPC ............................ 607/117; 607/118; 607/128
(58) Field of Classification Search
USPC .......................................... 607/116–118, 128
See application file for complete search history.

(56) References Cited

U.S. PATENT DOCUMENTS

| 3,650,276 A | 3/1972 | Burghele et al. |
| 3,902,501 A | 9/1975 | Citron et al. |
| 3,939,843 A | 2/1976 | Smyth |
| 4,033,357 A | 7/1977 | Helland et al. |

(Continued)

FOREIGN PATENT DOCUMENTS

| DE | 3146182 | 6/1983 |
| DE | 3415410 | 10/1984 |
| EP | 1181948 | 2/2002 |

OTHER PUBLICATIONS

Office Action dated Dec. 11, 2007 for U.S. Appl. No. 11/352,552 (7 pgs.).

(Continued)

*Primary Examiner* — Joseph Stoklosa
(74) *Attorney, Agent, or Firm* — Shumaker & Sieffert, P.A.

(57) ABSTRACT

An implantable medical electrical lead comprises a lead body extending between a distal end and a proximal end, and the distal end having at least one electrode of an electrode array extending longitudinally from the distal end toward the proximal end. The lead body at its proximal end may be coupled to a pulse generator, additional intermediate wiring, or other stimulation device. A fixation mechanism is formed on or integrally with the lead body proximal to the electrode array that is adapted to be implanted in and engage subcutaneous tissue, particularly muscle tissue, to inhibit axial movement of the lead body and dislodgement of the stimulation electrodes. The fixation mechanism comprises a plurality of tine elements arrayed in a tine element array along a segment of the lead.

24 Claims, 8 Drawing Sheets

(56) References Cited

U.S. PATENT DOCUMENTS

| | | | |
|---|---|---|---|
| 4,044,774 A * | 8/1977 | Corbin et al. | 607/117 |
| 4,236,529 A | 12/1980 | Little | |
| 4,262,678 A | 4/1981 | Stokes | |
| 4,269,198 A | 5/1981 | Stokes | |
| 4,289,144 A | 9/1981 | Gilman | |
| 4,301,815 A | 11/1981 | Doring | |
| 4,360,031 A | 11/1982 | White | |
| 4,393,883 A | 7/1983 | Smyth et al. | |
| 4,402,328 A | 9/1983 | Doring | |
| 4,402,329 A | 9/1983 | Williams | |
| 4,407,303 A | 10/1983 | Akerstrom | |
| 4,409,994 A | 10/1983 | Doring | |
| 4,414,986 A | 11/1983 | Dickhudt et al. | |
| 4,419,819 A | 12/1983 | Dickhudt et al. | |
| 4,432,377 A | 2/1984 | Dickhudt | |
| 4,437,475 A | 3/1984 | White | |
| 4,465,079 A | 8/1984 | Dickhudt | |
| 4,479,500 A | 10/1984 | Smits | |
| 4,488,561 A | 12/1984 | Doring | |
| 4,502,492 A | 3/1985 | Bomzin | |
| 4,506,679 A | 3/1985 | Mann | |
| 4,506,680 A | 3/1985 | Stokes | |
| 4,512,351 A * | 4/1985 | Pohndorf | 607/117 |
| 4,538,624 A | 9/1985 | Tarjan | |
| 4,564,023 A | 1/1986 | Hess | |
| 4,569,351 A | 2/1986 | Tang | |
| 4,577,642 A | 3/1986 | Stokes | |
| 4,590,949 A | 5/1986 | Pohndorf | |
| 4,606,118 A | 8/1986 | Cannon et al. | |
| 4,607,739 A | 8/1986 | Kaiser | |
| 4,658,835 A | 4/1987 | Pohndorf | |
| 4,711,251 A | 12/1987 | Stokes | |
| 4,716,888 A | 1/1988 | Wesner | |
| 4,739,764 A | 4/1988 | Lue et al. | |
| 4,771,779 A | 9/1988 | Tanagho et al. | |
| 4,796,643 A | 1/1989 | Nakazawa et al. | |
| 4,860,446 A | 8/1989 | Lessar et al. | |
| 4,883,070 A | 11/1989 | Hanson | |
| 4,913,147 A | 4/1990 | Fahlstrom et al. | |
| 4,920,979 A | 5/1990 | Bullara | |
| 4,922,927 A | 5/1990 | Fine et al. | |
| 4,945,922 A | 8/1990 | van Krieken | |
| 4,957,118 A * | 9/1990 | Erlebacher | 607/128 |
| 4,989,617 A * | 2/1991 | Memberg et al. | 607/116 |
| 5,040,544 A | 8/1991 | Lessar et al. | |
| 5,207,672 A | 5/1993 | Roth et al. | |
| 5,231,996 A | 8/1993 | Bardy et al. | |
| 5,257,634 A * | 11/1993 | Kroll | 607/122 |
| 5,282,844 A | 2/1994 | Stokes et al. | |
| 5,282,845 A | 2/1994 | Bush et al. | |
| 5,300,107 A | 4/1994 | Stokes et al. | |
| 5,313,953 A | 5/1994 | Yomtov et al. | |
| 5,336,253 A | 8/1994 | Gordon et al. | |
| 5,344,439 A | 9/1994 | Otten | |
| 5,376,108 A | 12/1994 | Collins et al. | |
| 5,385,577 A | 1/1995 | Maurer et al. | |
| 5,408,744 A | 4/1995 | Gates | |
| 5,411,545 A | 5/1995 | Breyen et al. | |
| 5,423,881 A | 6/1995 | Breyen et al. | |
| 5,433,744 A | 7/1995 | Breyen et al. | |
| 5,484,445 A | 1/1996 | Knuth | |
| 5,562,722 A | 10/1996 | Racz et al. | |
| 5,562,723 A | 10/1996 | Rugland et al. | |
| 5,578,068 A | 11/1996 | Laske et al. | |
| 5,653,742 A | 8/1997 | Parker et al. | |
| 5,733,322 A | 3/1998 | Starkebaum | |
| 5,755,767 A | 5/1998 | Doan et al. | |
| 5,796,044 A | 8/1998 | Cobian et al. | |
| 5,807,399 A | 9/1998 | Laske et al. | |
| 5,824,032 A | 10/1998 | Belden | |
| 5,827,296 A | 10/1998 | Morris et al. | |
| 5,843,149 A | 12/1998 | Ebert et al. | |
| 5,849,031 A | 12/1998 | Martinez et al. | |
| 5,885,258 A | 3/1999 | Sachdeva et al. | |
| 5,897,585 A | 4/1999 | Williams | |
| 5,902,330 A | 5/1999 | Ollivier et al. | |
| 5,902,331 A | 5/1999 | Bonner et al. | |
| 5,928,277 A | 7/1999 | Laske et al. | |
| 5,957,965 A | 9/1999 | Moumane et al. | |
| 5,957,966 A | 9/1999 | Schroeppel et al. | |
| 5,957,967 A | 9/1999 | Laske | |
| 5,957,970 A | 9/1999 | Shoberg et al. | |
| 5,968,086 A | 10/1999 | Bonner et al. | |
| 5,991,668 A | 11/1999 | Leinders et al. | |
| 6,006,139 A | 12/1999 | Kruse et al. | |
| 6,021,354 A | 2/2000 | Warman et al. | |
| 6,052,625 A | 4/2000 | Marshall | |
| 6,055,456 A | 4/2000 | Gerber | |
| 6,055,457 A | 4/2000 | Bonner | |
| 6,104,960 A | 8/2000 | Duysens et al. | |
| 6,149,678 A | 11/2000 | DiDomenico et al. | |
| 6,178,355 B1 | 1/2001 | Williams et al. | |
| 6,185,464 B1 | 2/2001 | Bonner et al. | |
| 6,240,322 B1 | 5/2001 | Peterfeso et al. | |
| 6,510,347 B2 * | 1/2003 | Borkan | 607/117 |
| 6,512,957 B1 | 1/2003 | Witte | |
| 6,832,115 B2 | 12/2004 | Borkan | |
| 6,999,819 B2 | 2/2006 | Swoyer et al. | |
| 7,239,924 B2 | 7/2007 | Kolberg | |
| 7,330,764 B2 | 2/2008 | Swoyer et al. | |
| 7,912,555 B2 | 3/2011 | Swoyer et al. | |
| 8,000,805 B2 | 8/2011 | Swoyer et al. | |
| 8,036,756 B2 | 10/2011 | Swoyer et al. | |
| 2004/0230279 A1 | 11/2004 | Cates et al. | |

OTHER PUBLICATIONS

Response to Office Action filed Apr. 11, 2008 for U.S. Appl. No. 11/352,552 (12 pgs.).
Office Action dated Oct. 31, 2008 for U.S. Appl. No. 11/352,552 (10 pgs.)
Responsive Amendment dated Dec. 31, 2008 for U.S. Appl. No. 11/352,552 (13 pgs.).
Office Action dated Mar. 11, 2009 for U.S. Appl. No. 11/352,552 (10 pgs.).
Request for Continued Examination and Responsive Amendment dated May 12, 2009 for U.S. Appl. No. 11/352,552 (13 pgs.).
Office Action dated Jun. 11, 2009 for U.S. Appl. No. 12/023,817 (11 pgs.).
Responsive Amendment dated Aug. 11, 2009 for U.S. Appl. No. 12/023,817 (12 pgs.).
Office Action dated Jul. 6, 2009 for U.S. Appl. No. 11/352,552 (9 pgs.).
U.S. Appl. No. 12/023,817, filed Jan. 31, 2008, "Implantable Medical Electrical Stimulation Lead Fixation Method and Apparatus,".
Response dated Oct. 6, 2009 for U.S. Appl. No. 11/352,552 (7 pgs.).
Office Action dated Dec. 29, 2009 for U.S. Appl. No. 11/352,552 (8 pgs.).
Office Action dated Oct. 27, 2009 for U.S. Appl. No. 12/023,817 (9 pgs.).
Responsive Amendment dated Jan. 27, 2010 for U.S. Appl. No. 12/023,817 (8 pgs.).
Responsive Amendment dated Mar. 29, 2010 for U.S. Appl. No. 11/352,552 (10 pgs.).
Office Action dated Jul. 7, 2010 for U.S. Appl. No. 11/352,552 (10 pgs.).
Responsive Amendment dated Sep. 7, 2010 for U.S. Appl. No. 11/352,552 (12 pgs.).
Office Action dated Nov. 15, 2010 for U.S. Appl. No. 11/352,552, (5 pgs.).
Responsive Amendment dated Feb. 15, 2011 for U.S. Appl. No. 11/352,552, (15 pgs.).
Office Action dated Jun. 1, 2009 for U.S. Appl. No. 11/589,407, (13 pgs.).
Responsive Amendment dated Sep. 1, 2009 for U.S. Appl. No. 11/589,407, (13 pgs.).
Office Action dated Dec. 29, 2009 for U.S. Appl. No. 11/589,407, (9 pgs.).
Response dated Feb. 26, 2010 for U.S. Appl. No. 11/589,407, (7 pgs.).

(56) References Cited

OTHER PUBLICATIONS

Advisory Action dated Mar. 31, 2010 for U.S. Appl. No. 11/589,407, (4 pgs.).
Final Office Action dated Nov. 16, 2010 for U.S. Appl. No. 11/589,407, (7 pgs.).
Request for Continued Examination and Responsive Amendment dated Feb. 16, 2011 for U.S. Appl. No. 11/589,407, (10 pgs.).
Restriction Requirement dated Aug. 29, 2003 for U.S. Appl. No. 10/004,732, (4 pgs.).
Response dated Sep. 25, 2003 for U.S. Appl. No. 10/004,732, (2 pgs.).
Office Action dated Jan. 16, 2004 for U.S. Appl. No. 10/004,732, (8 pgs.).
Response dated Mar. 15, 2004 for U.S. Appl. No. 10/004,732, (10 pgs.).
Final Office Action dated May 4, 2004 for U.S. Appl. No. 10/004,732, (9 pgs.).
Request for Continued Examination and Responsive Amendment dated Jul. 29, 2004 for U.S. Appl. No. 10/004,732, (7 pgs.).
Office Action dated Nov. 3, 2004 for U.S. Appl. No. 10/004,732, (9 pgs.).
Response dated Feb. 3, 2005 for U.S. Appl. No. 10/004,732, (6 pgs.).
Final Office Action dated Jun. 16, 2005 for U.S. Appl. No. 10/004,732, (9 pgs.).
Response dated Aug. 16, 2005 for U.S. Appl. No. 10/004,732, (11 pgs.).

* cited by examiner

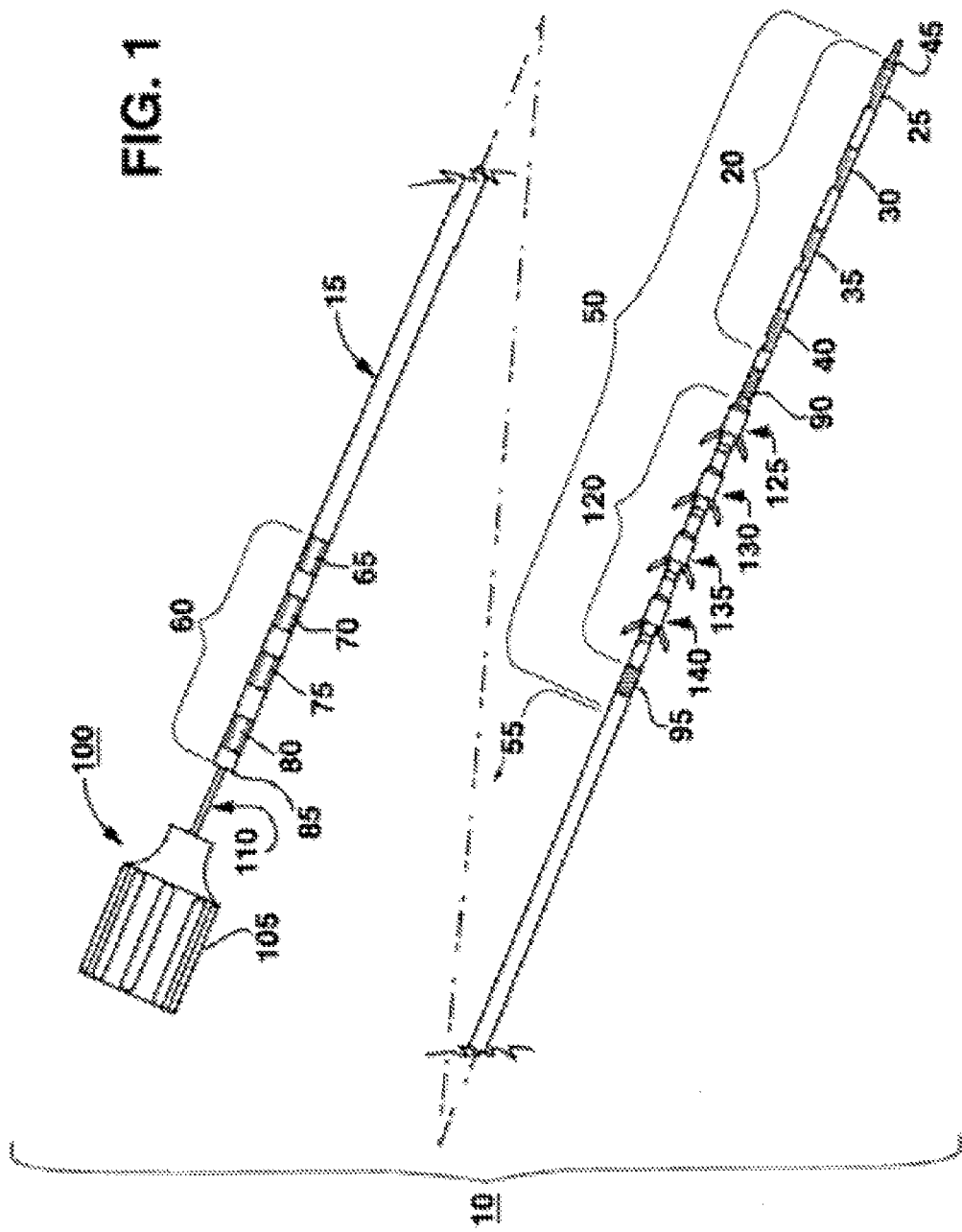

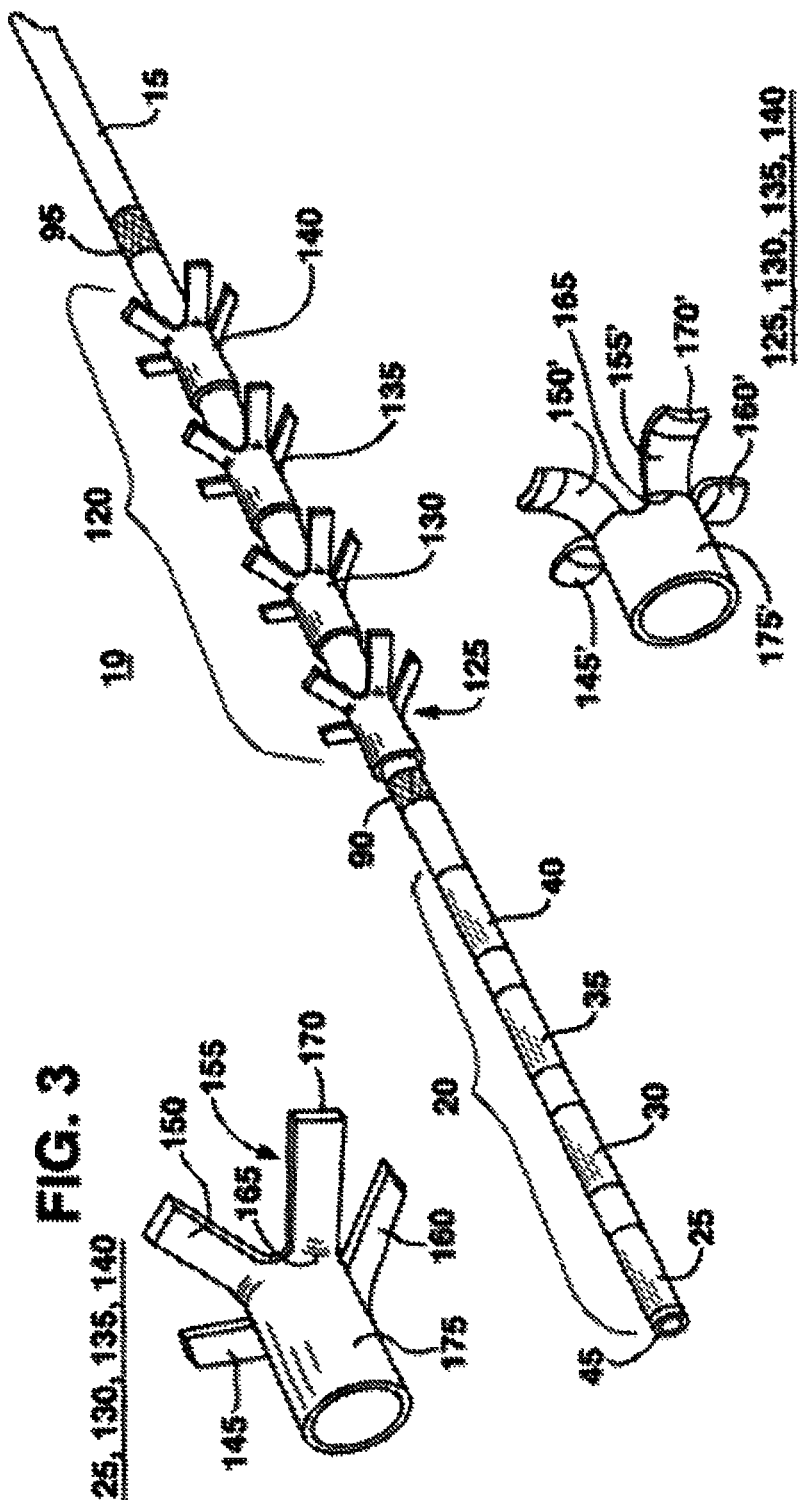

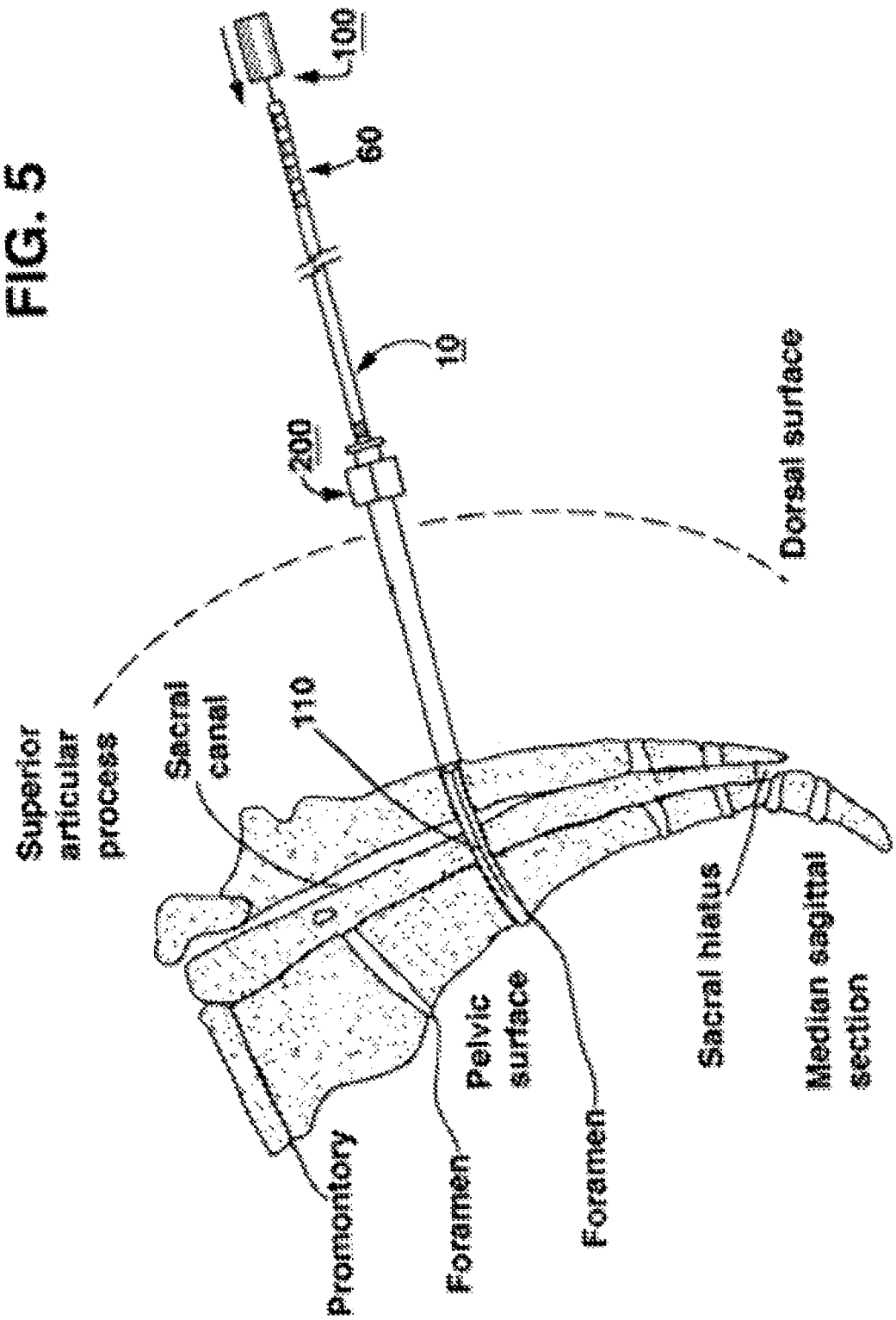

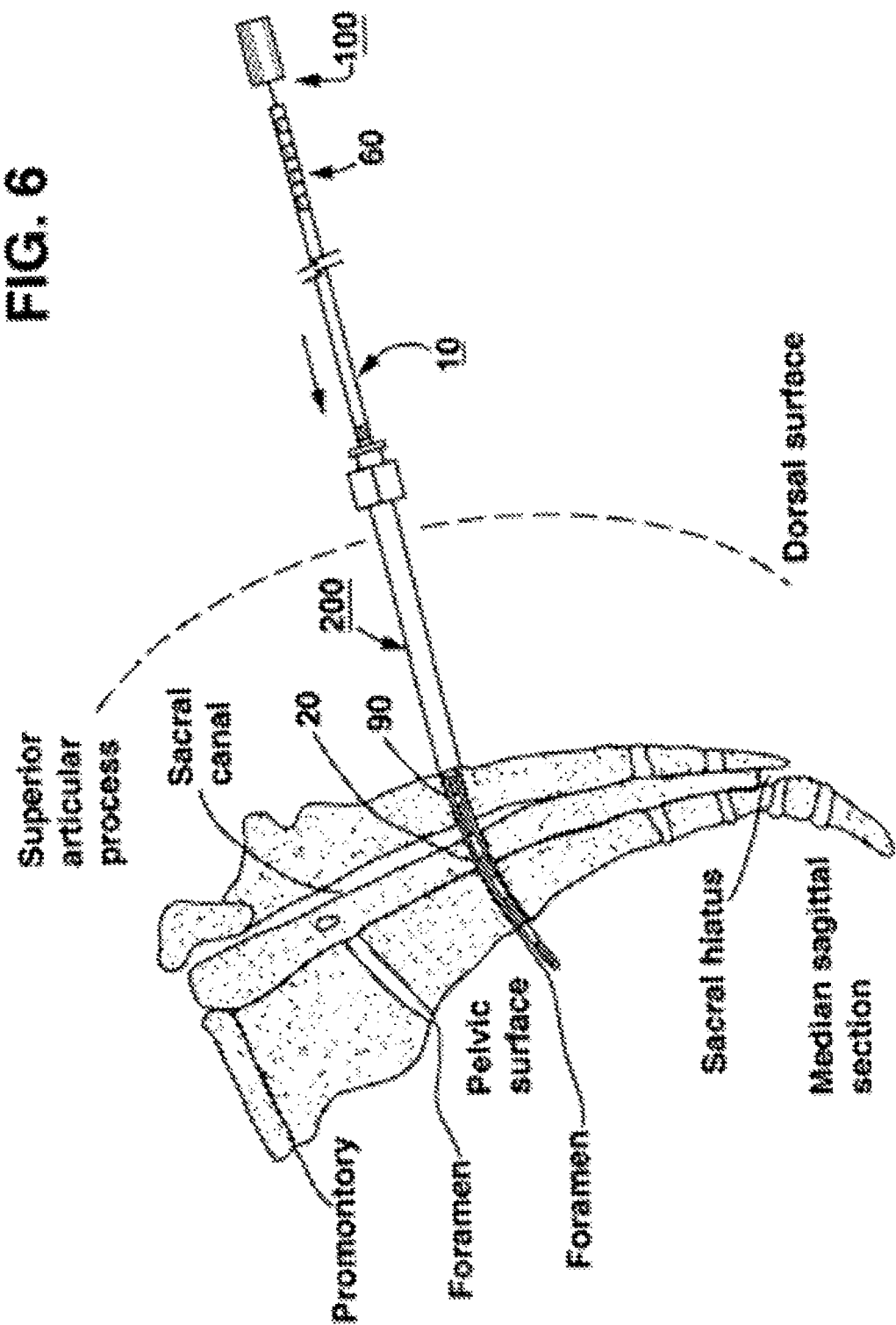

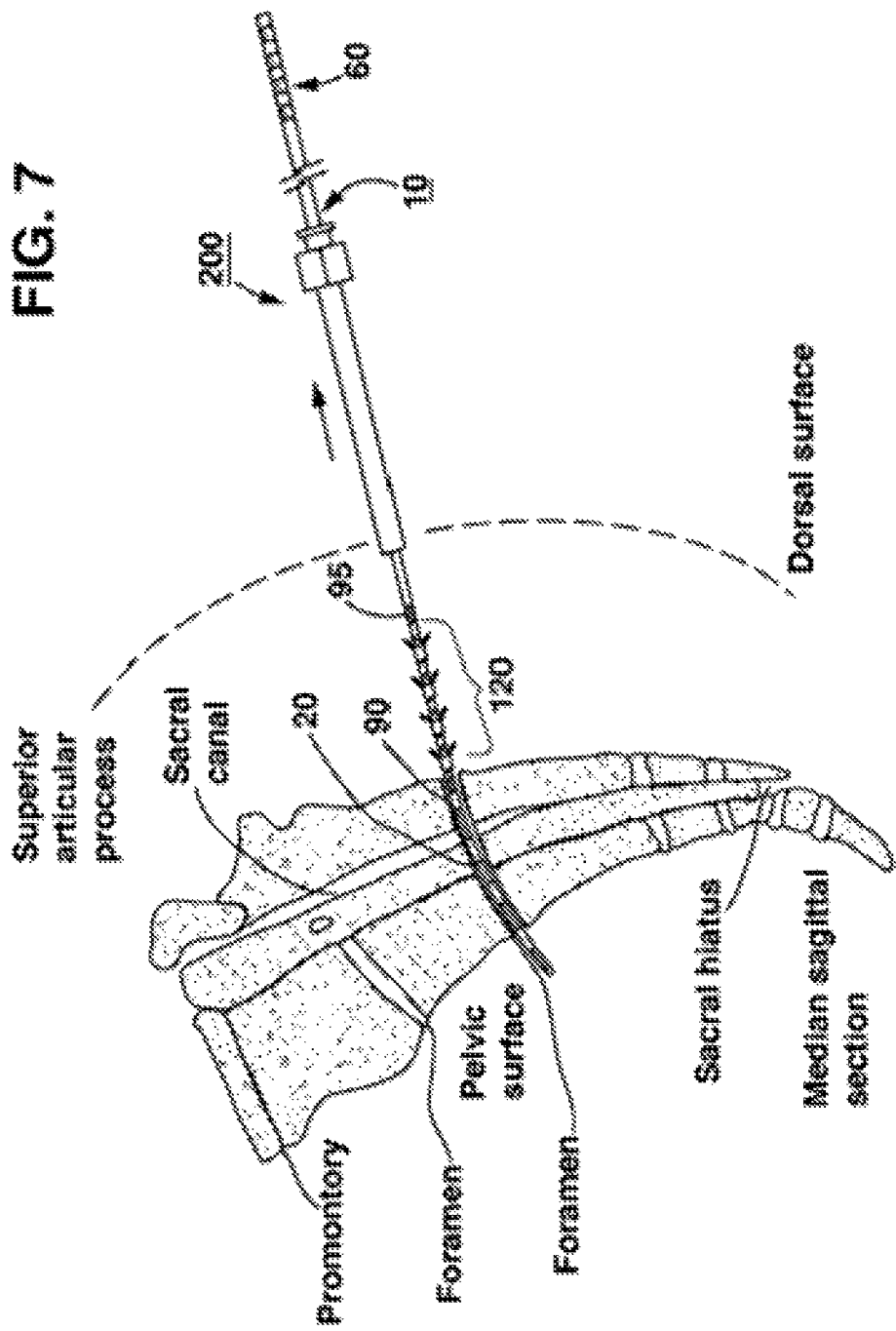

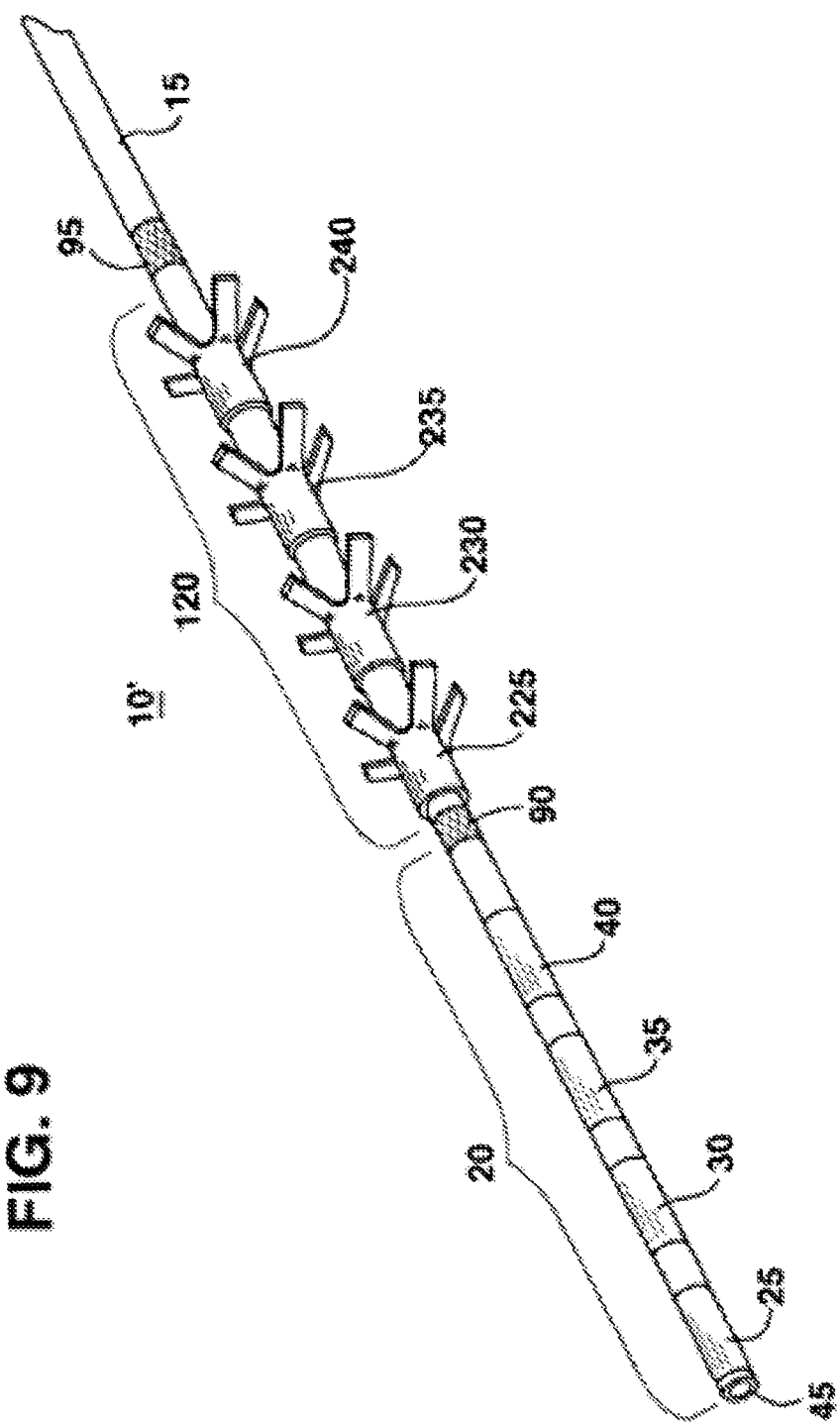

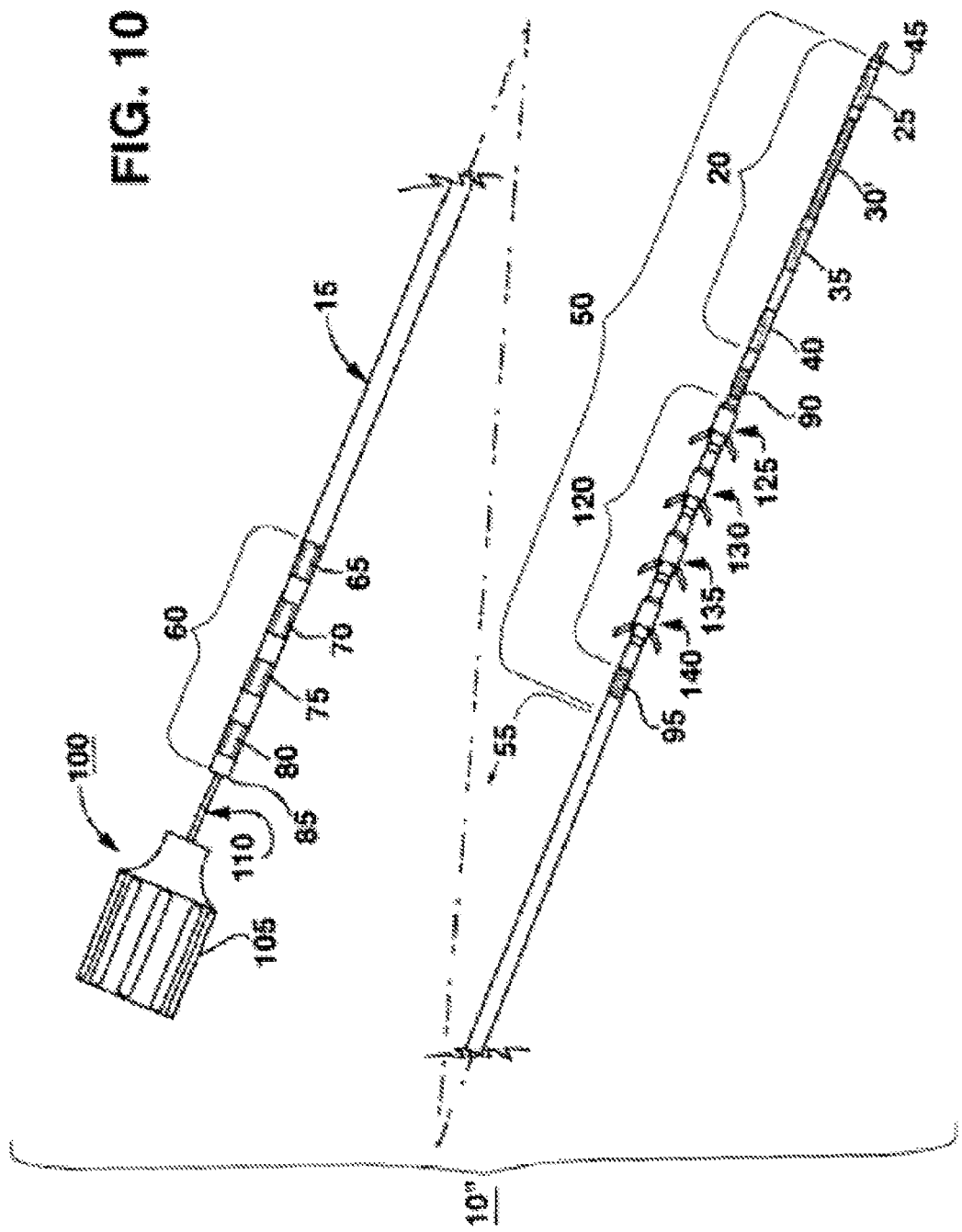

IMPLANTABLE MEDICAL LEAD INCLUDING A PLURALITY OF TINE ELEMENTS

RELATED APPLICATIONS

This application is a continuation of U.S. patent application Ser. No. 11/589,407 by Swoyer et al., filed Oct. 30, 2006 and entitled, "Implantable Medical Lead Including Tine Markers," which is a continuation of U.S. patent application Ser. No. 11/352,552 by Swoyer et al., filed on Feb. 13, 2006 and entitled, "Implantable Medical Electrical Stimulation Lead Fixation Method and Apparatus." U.S. patent application Ser. No. 11/352,552 by Swoyer et al. is a continuation of U.S. patent application Ser. No. 10/004,732 by Swoyer et al., filed Nov. 9, 2001 and entitled, "Implantable Medical Electrical Stimulation Lead Fixation Method And Apparatus," which claims the benefit of U.S. Provisional Patent Application No. 60/316,582, filed Aug. 31, 2001. U.S. patent application Ser. No. 11/589,407 published as U.S. Patent Application Publication No. 2007/0050004 on Mar. 1, 2007. U.S. patent application Ser. No. 11/352,552 published as U.S. Patent Application Publication No. 2006/0129218 on Jun. 15, 2006. U.S. patent application Ser. No. 10/004,732 issued as U.S. Pat. No. 6,999,819 to Swoyer et al. on Feb. 14, 2006. The entire content of U.S. Patent Application Publication Nos. 2007/0050004 and 2006/0129218, U.S. Pat. No. 6,999,819, and U.S. Provisional Patent Application No. 60/316,582 is incorporated herein by reference.

BACKGROUND OF THE INVENTION

1. Field of the Invention

This invention relates generally to a method and apparatus that allows for stimulation of body tissue, particularly sacral nerves. More specifically, this invention relates to an implantable medical electrical lead having at least one stimulation electrode adapted to be implanted near the sacral nerves for stimulation of a bundle of sacral nerve fibers and a fixation mechanism for providing chronic stability of the stimulation electrode and lead. Moreover, this invention relates to the method of implantation and anchoring of the medical electrical lead electrodes in operative relation to a selected sacral nerve to allow for stimulation.

2. Description of Related Art

Pelvic floor disorders such as, urinary incontinence, urinary urge/frequency, urinary retention, pelvic pain, bowel dysfunction (constipation, diarrhea), erectile dysfunction, are bodily functions influenced by the sacral nerves. Specifically, urinary incontinence is the involuntary control over the bladder that is exhibited in various patients. Incontinence is primarily treated through pharmaceuticals and surgery. Many of the pharmaceuticals do not adequately resolve the issue and can cause unwanted side effects, and a number of the surgical procedures have a low success rate and are not reversible. Several other methods have been used to control bladder incontinence, for example, vesicostomy or an artificial sphincter implanted around the urethea. These solutions have drawbacks well known to those skilled in the art. In addition, some disease states do not have adequate medical treatments.

The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum. The sacrum, generally speaking, is a large, triangular bone situated at the lower part of the vertebral column, and at the upper and back part of the pelvic cavity. The spinal canal runs throughout the greater part of the sacrum. The sacrum is perforated by the anterior and posterior sacral foramina that the sacral nerves pass through.

Neurostimulation leads have been implanted on a temporary or permanent basis having at least one stimulation electrode positioned on and near the sacral nerves of the human body to provide partial control for bladder incontinence. Temporary sacral nerve stimulation is accomplished through implantation of a temporary neurostimulation lead extending through the skin and connected with a temporary external pulse generator as described for example in commonly assigned U.S. Pat. Nos. 5,957,965 and 6,104,960. A permanent neurostimulator is implanted if stimulation is efficacious and it is possible to do so in the particular patient. Permanent implantation is accomplished by implanting a permanent neurostimulation lead, extending the proximal portion of the lead body subcutaneously, and connecting its proximal end with an implantable pulse generator (IPG) implanted subcutaneously.

For example, U.S. Pat. Nos. 4,771,779, 4,607,739 and 4,739,764 disclose implanting an electrode on at least one nerve controlling the bladder and applying nerve stimulation energy to the nerve through the electrode. Electrodes positioned within the sacrum to control bladder function are also disclosed in U.S. Pat. No. 4,569,351.

In one embodiment, a lead bearing a distal stimulation electrode is percutaneously implanted through the dorsum and the sacral foramen (a singular foramina) of the sacral segment S3 for purposes of selectively stimulating the S3 sacral nerve. The lead is advanced through the lumen of a hollow spinal needle extended through the foramen, the single distal tip electrode is positioned adjoining the selected sacral nerve. Stimulation energy is applied through the lead to the electrode to test the nerve response. The electrode is moved back and forth to locate the most efficacious location, and the lead is then secured by suturing the lead body to subcutaneous tissue posterior to the sacrum and attached to the output of a neurostimulator IPG. Despite the suture fixation, sacral nerve stimulation leads having a single discrete tip electrode can be dislodged from the most efficacious location due to stresses placed on the lead by the ambulatory patient. A surgical intervention is then necessary to reposition the electrode and affix the lead.

The current lead designs used for permanent implantation to provide sacral nerve stimulation through a foramen have a number, e.g., four, ring-shaped, stimulation electrodes spaced along a distal segment of the lead body adapted to be passed into or through the foramen along a selected sacral nerve. Each distal stimulation electrode is electrically coupled to the distal end of a lead conductor within the elongated lead body that extends proximally through the lead body. The proximal ends of the separately insulated lead conductors are each coupled to a ring-shaped connector element in a proximal connector element array along a proximal segment of the lead body that is adapted to be coupled with the implantable neurostimulation pulse generator or neurostimulator IPG.

Again, the electrode array is moved back and forth with respect to the sacral nerve while the response to stimulation pulses applied through one or more of the electrodes is determined. The IPG is programmed to deliver stimulation pulse energy to the electrode providing the optimal nerve response, and the selection of the electrodes can be changed if efficacy using a selected electrode fades over time due to dislodgement or other causes.

Electrical stimulation pulses generated by the neurostimulator IPG are applied to the sacral nerve through the selected one or more of the stimulation electrodes in either a unipolar or bipolar stimulation mode. In one unipolar stimulation mode, the stimulation pulses are delivered between a selected active one of the stimulation electrodes and the electrically conductive, exposed surface of the neurostimulator IPG housing or can providing a remote, indifferent or return electrode. In this case, efficacy of stimulation between each stimulation electrode and the neurostimulator IPG can electrode is tested, and the most efficacious combination is selected for use. In a further unipolar stimulation mode, two or more of the stimulation electrodes are electrically coupled together providing stimulation between the coupled together stimulation electrodes and the return electrode.

In a bipolar stimulation mode, one of the distal stimulation electrodes is selected as the indifferent or return electrode. Localized electrical stimulation of the sacral nerve is effected between the active stimulation electrode(s) and the indifferent stimulation electrode.

A problem associated with implantation of permanent and temporary neurostimulation leads involves maintaining the discrete ring-shaped electrode(s) in casual contact, that is in location where slight contact of the electrode with the sacral nerve may occur or in close proximity to the sacral nerve to provide adequate stimulation of the sacral nerve, while allowing for some axial movement of the lead body.

Typically, physicians spend a great deal of time with the patient under a general anesthetic placing the leads due to the necessity of making an incision exposing the foramen and due to the difficulty in optimally positioning the small size stimulation electrodes relative to the sacral nerve. The patient is thereby exposed to the additional dangers associated with extended periods of time under a general anesthetic. Movement of the lead, whether over time from suture release or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation that, in turn, requires consistent presence of the stimulation electrode proximate the sacral nerve. But, too close or tight a contact of the electrode with the sacral nerve can also cause inflammation or injury to the nerve diminishing efficacy and possibly causing patient discomfort.

Once the optimal electrode position is attained, it is necessary to fix the lead body to retard lead migration and dislodgement of the electrodes from the optimal position employing sutures or a sacral lead fixation mechanism of the types described in the above-referenced '351 patent or an improved fixation mechanism of the type described in commonly assigned U.S. Pat. No. 5,484,445. However, it is desirable to avoid use of complex fixation mechanisms that require surgical exposure large enough to implant the fixation mechanism, in these cases requiring exposure and attachment to the sacrum.

Once fixation is completed, the proximal lead body is typically bent at about 90° and tunneled subcutaneously to a remote site where its proximal connector elements are coupled to the neurostimulator IPG which is then implanted at the remote site. In this process some axial and lateral dislodgement of the stimulation electrodes can also occur.

It is generally desirable to minimize surgical trauma to the patient through surgical exposure of the tissue and sacrum and use of sutures or fixation mechanisms to hold the electrodes in place. It is preferred to employ a minimally invasive, percutaneous approach in a path extending from the skin to the foramen that the neurostimulation lead is extended through.

The above-referenced '965 patent describes one such percutaneous approach for implantation of a temporary neurostimulation lead that extends through the patient's skin and is attached to an external pulse generator. Typically, the external pulse generator and exposed portion of the lead body are taped to the skin to inhibit axial movement of the lead body. When a stimulation time period ends, the lead is removed through the skin by application of traction to the exposed lead body, and the incision is closed. The neurostimulation lead bodies of the '965 patents are formed with surface treatment or roughening in a portion proximal to the neurostimulation electrode expected to extend from the foramen to the patient's skin that is intended to increase the resistance to unintended axial dislodgement of the lead body to stabilize the electrode. A length of the lead body is formed with indentations or spiral ridges or treated to have a macroscopic roughening. These surface treatments or geometries provide some acute fixation against the subcutaneous tissues, but they are necessarily insufficient to resist intentional retraction of the lead to remove it upon cessation of temporary stimulation.

The prior art discloses a number of configurations of implantable medical electrical leads other than neurostimulation leads that employ fixation mechanisms to maintain a stimulation electrode in relation to a body organ or tissue. Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known in the art as exemplified by U.S. Pat. Nos. 3,902,501, 3,939,843, 4,033,357, 4,236,529, 4,269,198, 4,301,815, 4,402,328, 4,409,994, and 4,883,070, for example. Such tined leads typically employ three or four tines that extend outwardly and proximally from a band proximal to a distal tip pace/sense electrode and that catch in natural trabecular interstices when the distal tip electrode is advanced into the atrial appendage or the ventricular apex. Certain spinal cord stimulation leads have been proposed employing tines and/or vanes as stand-offs to urge the stimulation electrode in the epidural space toward the spinal cord as disclosed in U.S. Pat. Nos. 4,590,949 and 4,658,535, for example, and to stabilize the stimulation electrode in the epidural space as disclosed in U.S. Pat. No. 4,414,986, for example, In the case of the '843 patent that was directed to the first atrial tined leads, longitudinally extending rows of elongated tines were provided within a 270° arc extending away from a distal tip electrode canted in the remaining 90° section. The multiple rows of tines were intended to lodge in the trabecular interstices and force the canted tip against the atrial endocardial wall. However, it was found in practice that the canted tip is unnecessary and that only three, much shorter, tines in the 270° arc or four tines spaced apart by 90° in a common circumference like a ventricular tined lead, are sufficient. The rows of tines shown in the '843 patent are necessarily closely spaced because of the small area of trabeculae in the right atrium, and more proximal tines simply typically do not engage anything and make it difficult to lodge any of the tines in the interstitial spaces.

Such endocardial tined leads are typically introduced from a puncture site of the venous system to the cardiac site employing a stiffening stylet with a tip that can be formed with a curve extended down the lead lumen to advance it through the venous system and into the heart chamber. Percutaneous lead introducers are used to access the puncture site. The tines fold against the introducer lumen and the vein wall after the lead distal end exits the introducer lumen. However, the above-referenced '070 patent does describe thin, webbed, or scalloped tines adapted to be introduced through an introducer already advanced all the way into a heart chamber.

In certain cases, sensing leads that include electrogram (EGM) sense electrodes are implanted subcutaneously and coupled to implantable cardiac monitors. One such cardiac monitoring system as shown in U.S. Pat. No. 5,313,953, for example, employs elongated electrode supports at the distal ends of leads that are tunneled subcutaneously into a sense electrode array and affixed with sutures sewn through preformed suture holes to subcutaneous tissue. First and second rows of projections also extend outwardly and proximally from the opposed first and second side walls of the electrode supports whereby the projections are in a common plane with the sense electrode. It is expected that tissue growth will occur around the projections and stabilize the lead. However, it can also be seen that the leads are advanced subcutaneously between tissue layers expanded by tunneling. The projections would likely not engage tissue during the acute phase before they are encapsulated. For this reason, the elongated leads are sutured in place to maintain the electrode position until the projections are encapsulated by tissue ingrowth. Furthermore, it is less critical to maintaining exact positioning of the sense electrodes of such a subcutaneous cardiac monitor than maintaining stimulation electrodes in the implanted positions for cardiac or nerve or muscle stimulation because minute stimulation electrode movement can decrease efficacy and increase battery energy consumption or fail.

Accordingly, there remains a need in the art for a permanently implantable electrical sacral nerve stimulation lead that is capable of being passed percutaneously over a guide wire, and/or through the lumen of an introducer from the patient's skin to locate stimulation electrodes in casual contact with a sacral nerve, that provides acute fixation with muscle and tissue layers posterior to the sacrum, and that can be bent to extend subcutaneously to the neurostimulator IPG without disturbing the fixation so that the stimulation electrodes are less likely to be dislodged during the acute recovery phase and the chronic implantation period.

SUMMARY OF THE INVENTION

The present invention recognizes and provides a solution to the problems associated with implanting and maintaining electrical leads in body tissue, particularly muscle tissue to maintain one or more lead electrode in relation to a particular body site, through use of minimally invasive implantation techniques. In a preferred embodiment, the present invention maintains one or more sacral nerve stimulation electrode in close proximity or casual contact with discrete nerve fibers of the sacral nerves by providing a unique solution that allows minimally invasive, percutaneous, implantation near to, but avoiding compressive contact with, the sacral nerves and fixation of the lead body in subcutaneous tissues. Additionally, the invention provides apparatus and a method of implanting a medical electrical stimulation lead through the subcutaneous tissue and foramen for stimulating a bundle of nerve fibers of the sacral nerve anterior to the sacral nerve opening through the sacrum.

Briefly, preferred embodiments of the present invention comprise a permanently implantable lead comprising a distal electrode that is maintained at a site in the body by a fixation mechanism that is formed on or integrally with the lead proximal to the electrode that is adapted to be implanted in and engage subcutaneous tissue, particularly muscle tissue, to inhibit axial movement of the lead body and dislodgement of the stimulation electrode. The fixation mechanism comprises a plurality M of tine elements arrayed in a tine element array along a segment of the lead proximal to the stimulation electrode array. Each tine element comprises at least N flexible, pliant, tines, each tine having a tine width and thickness and extending through a tine length from an attached tine end to a free tine end. The attached tine end is attached to the lead body from a tine attachment site and supports the tine extending radially from the lead body and proximally toward the lead proximal end. The M×N tines are adapted to be folded inward against the lead body when fitted into and constrained by the lumen of an introducer such that the tine length is folded up against lead body, and the folded tines do not overlap one another.

A particular embodiment of the present invention comprises a permanently implantable neurostimulation lead adapted to be advanced percutaneously from a skin incision to the selected foramen of the sacrum wherein the tines of the tine elements engage muscle tissue between the incision and the foramen to inhibit retraction of the neurostimulation lead. The neurostimulation lead preferably comprises P distally disposed stimulation electrodes, where P=one or more, arranged in an electrode array spaced apart from one another along a distal segment of the lead body adapted to be inserted into the selected foramen. Each stimulation electrode is electrically coupled to the distal end of a lead conductor within the elongated lead body that extends proximally through the lead body. The proximal ends of the separately insulated lead conductors are coupled to one of P respective connector elements in a proximal connector element array along a proximal segment of the lead body adjacent the lead proximal end that are adapted to be coupled with a neurostimulator IPG. Electrical stimulation pulses generated by the neurostimulator IPG are applied to the sacral nerve through one or more of the P stimulation electrodes in either a unipolar or bipolar stimulation mode.

Preferably, each of the M tine elements comprises a plurality N tines extending from respective attached tine ends disposed apart from one another, preferably, but not necessarily, equally spaced apart, along a common circumference extending around the lead body. The N tine attachment points around the common circumference for a distal tine element are preferably offset radially from the N tine attachment points around the common circumference of the adjacent proximal tine element. This distribution insures that the retention forces exerted against the muscle layers by the tines are distributed more uniformly around the lead body than would be the case if the tines were in parallel rows along the length of the lead body. In this embodiment, the tine lengths can be longer than the distance between the common circumferences of the proximal and distal tine elements along the lead body length. The N tines of each more distal tine element can be interleaved between the N tines of each more proximal tine element when constrained within an introducer lumen.

In another embodiment, each of the M tine elements comprises a tine mounting band encircling the lead body with the N tines extending from respective attached tine ends disposed apart from one another, preferably at equal spacing, around the tine mounting band. The N tines have a tine thickness that enables folding of the tines against the lead body in the space between the tine mounting band and the adjoining proximal tine mounting band.

In accordance with methods of implantation of the present invention, the tines of the tine element array along the length of the lead body are folded against the lead body when the stimulation electrode array and the tine element array are inserted into the lumen of an introducer. Preferably, a stiffening stylet is inserted through a lead body lumen to stiffen the lead as it is advanced into and through the introducer lumen.

The folded tines attempt to resume their unrestrained angle proximally away from the lead body when the lead is released from the distal lumen end opening of the introducer lumen. The tines resist being folded or inverted distally and present a folded cross-section profile that exceeds the lumen diameter inhibiting retraction proximally back through the distal lumen end opening of the introducer lumen.

During introduction, an introducer and an internally disposed element are advanced percutaneously to the foramen at a selected angle, and the inner element is then removed. The lead, optionally stiffened by a stiffening stylet disposed in the lead lumen, is advanced through the introducer lumen proximal end opening into the introducer lumen. Alternatively, the introducer with the distal segment of the lead body including the electrode array and the tine element array lead disposed within the introducer lumen is advanced percutaneously at a selected angle until the introducer distal end is disposed at the selected foramen. The advancement is optionally over a guide wire previously percutaneously advanced from the skin incision into the foramen to establish the angle of advancement or with a stiffening stylet disposed in the lead body lumen. In either approach, the stimulation electrode array and the tine element array are disposed within the introducer lumen pre-positioned to be implanted in relation to the sacral nerve and in the subcutaneous tissue, respectively. Both visual and radiographic markers are optionally disposed along the introducer, the guide wire, and/or the lead body to assist in pre-positioning the lead for implantation.

The distal portion of the neurostimulation lead is then advanced distally out of the introducer lumen distal end opening to advance the stimulation electrode array lead through the foramen from the posterior entrance into casual contact with the more anterior sacral nerve. The positioning is observed employing radiographic imaging and visual observation of a proximal marker on the lead body aligned with the introducer proximal hub. The introducer is retracted proximally after electrical testing to establish optimal positioning is completed, whereby the distal-to-proximal tine elements are successively released from the introducer lumen distal end opening. When the tines of each tine element are released in subcutaneous tissue, they bear against the tissue and inhibit proximal retraction of the lead body through the subcutaneous tissue if traction is applied to the lead body since the tines resist inversion in the proximal direction. The introducer and lead stylet, if present, are completely removed, and the proximal portion of the lead body is bent laterally with respect to the distal portion of the lead body and implanted through a subcutaneously tunneled path to the neurostimulator IPG.

The tines engage subcutaneous muscle layers that are penetrated by the introducer, not a pre-existing anatomical structure or a subcutaneously tunneled space overlying muscle layers. The tines are designed specifically to engage the muscle tissue and are relatively short and stiffer than the soft, pliant tines or projections on endocardial leads that get entangled in the trabeculae. Short, stiff tines provide better acute fixation in the muscle layers, and relatively harp, non-tapered, tine edges are provided to "dig into" the muscle.

In an alternative embodiment, one or more or all of the P stimulation electrodes is preferably formed of a flexible elongated mesh or wire coil electrodes that can bend somewhat to fit through a foramen to locate the elongated electrode optimally with respect to a sacral nerve. The elongated electrode surface area of the mesh or coiled wire electrode creates a wider electric field which allows the lead to be placed in a less precise or gross manner while still providing adequate electrical stimulation to the sacral nerve.

Accordingly, the present invention advantageously provides a unique implantable medical neurostimulation lead that provides adequate stimulation of the sacral nerves for control of incontinence and other pelvic floor disorders with the sacral nerves and with less sensitivity to placement and dislodgement. The unique lead simplifies the implant procedure and reduces or eliminates the need to reprogram the implantable pulse generator stimulation levels or re-open the patient to re-position the stimulation electrodes since the electrodes are less likely to move.

The implantation method for implanting the lead of the present invention allows more rapid placement of the electrodes for the treatment of incontinence whereby the lead is placed near the sacral nerves. Implanting the medical electrical lead near the sacral nerves with less specificity as to location near the sacral nerves reduces the time for implantation. Currently, the implantation procedure for existing medical electrical leads stimulating the sacral nerve fibers takes approximately 20-60 minutes. The present invention allows for implantation near the sacral nerve bundle and reduces the time for implantation to approximately 5-10 minutes.

The full range of advantages, and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Preferred embodiments of the invention are illustrated in the drawings, wherein like reference numerals refer to like elements in the various views, and wherein:

FIG. 1 is a plan view of one embodiment of sacral nerve stimulation lead of the present invention having a tine element array and stimulation electrode array in a distal portion of the lead body;

FIG. 2 is an expanded perspective view of the tine element array and stimulation electrode array in the distal portion of the lead body of FIG. 1;

FIG. 3 is an expanded perspective view of one embodiment of a tine element employed in the lead of FIGS. 1 and 2;

FIG. 4 is an expanded perspective view of a further embodiment of a tine element employed in the lead of FIGS. 1 and 2;

FIG. 5 is a cross-section view of the sacrum schematically illustrating an initial step of implanting a sacral nerve stimulation lead of the present invention with tines constrained within an introducer lumen;

FIG. 6 is a cross-section view of the sacrum schematically illustrating a further step of implanting a sacral nerve stimulation lead of the present invention extending the stimulation electrodes through a foramen;

FIG. 7 is a cross-section view of the sacrum schematically illustrating a further step of implanting a sacral nerve stimulation lead of the present invention retracting the introducer to release the tines in subcutaneous tissue;

FIG. 9 is an expanded perspective view of an alternative tine element array that can be substituted for the tine element array depicted in FIGS. 1 and 2; and FIG. 10 is a plan view of one embodiment of sacral nerve stimulation lead of the present invention having a tine element array and stimulation electrode array employing an elongated flexible electrode in a distal portion of the lead body.

DESCRIPTION OF THE PREFERRED EMBODIMENTS

Figure 8:
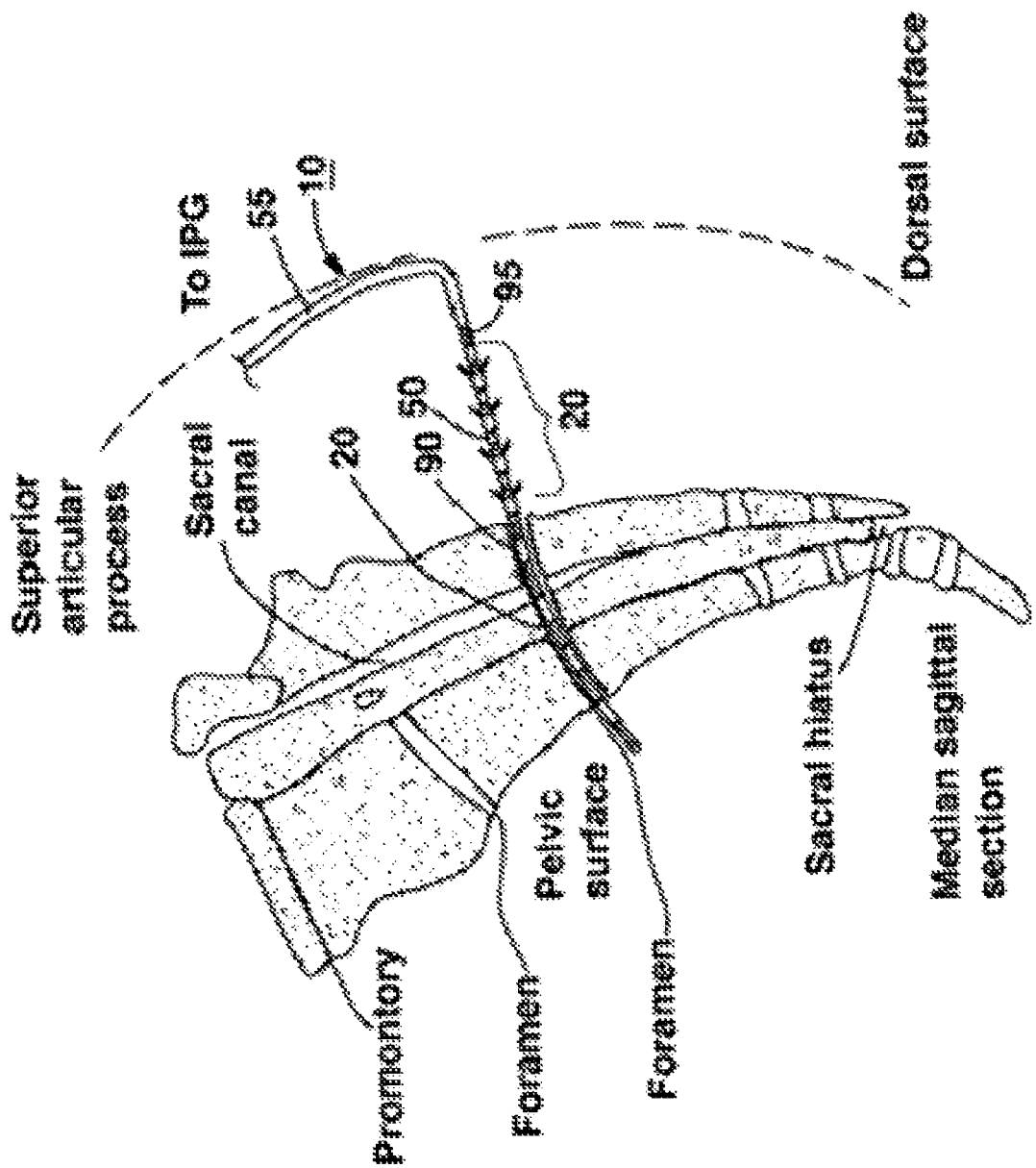
FIG. 8 is a cross-section view of the sacrum schematically illustrating a further step of implanting a sacral nerve stimulation lead of the present invention subcutaneously routing the proximal portion of the lead body to the implantation site of the neurostimulator IPG.

Referring to FIGS. 1 and 2, an implantable medical lead 10 preferably for sacral nerve stimulation that allows for non-direct contact stimulation of the sacral nerves comprises a lead body 15, wherein P=four, for example, ring-shaped electrodes 25, 30, 35, and 40 in an electrode array 20 extending proximally from the lead distal end 45. The lead body outer diameter is preferably in the range of about 0.5 mm to about 2 mm, and the lead 10 is preferably about 28.0 cm long. The electrode array 20 extends proximally longitudinally for a length of about 25.0 mm from the distal end 45. In one preferred embodiment, the electrodes 25, 30, 35 and 40 are made of a solid surface, bio-compatible material, e.g., a tube formed of platinum, platinum-iridium alloy, or stainless steel, of about 3.0 mm in length that does not degrade when electrical stimulation is delivered through it separated by shorter insulator bands.

Each stimulation electrode 25, 30, 35, and 40 is electrically coupled to the distal end of a coiled wire lead conductor within the elongated lead body 15 that extends proximally through the distal portion 50 and through the proximal portion 55 of the lead body 15. The proximal ends of the separately insulated lead conductors are each coupled to respective ring-shaped connector elements 65, 70, 75, and 80 in a proximal connector element array 60 along the proximal portion 55 of the lead body 15 adjacent the lead proximal end 85. The conductor wires are preferably formed of an MP35N alloy and are insulated from one another within an insulating polymer sheath such as polyurethane, fluoropolymer or silicone rubber. A typical diameter of the lead body 15 is 1.3 mm but a smaller diameter is also acceptable. The lead conductor wires are separately insulated by an insulation coating and are wound in a quadra-filar manner having a common winding diameter within the outer sheath. The coil formed by the coiled wire conductors defines a lead body lumen of the lead body 15. It will be understood that a further inner tubular sheath could be interposed within the aligned wire coils to provide the lead body lumen.

The connector elements 65, 70, 75, and 80 are adapted to be coupled with a neurostimulator IPG, additional intermediate wiring, or other stimulation device adapted to be implanted subcutaneously. An example of such an implantable pulse generator is the Medtronic InterStim Neurostimulator Model 3023. Electrical stimulation pulses generated by the neurostimulator IPG are applied to the sacral nerve through one or more of the stimulation electrodes 25, 30, 35 and 40 in either a unipolar or bipolar stimulation mode.

The axial lead body lumen (not shown) extends the length of the lead body 15 between a lumen proximal end opening at lead proximal end 85 and a lumen distal end opening at lead distal end 45. The straight wire 110 attached to the handle 105 of a guide wire or stiffening stylet 100 can be inserted through the lead body lumen to assist in implanting the lead 10 as described further below. The stylet wire 110 is preferably made of solid wire such as tungsten or stainless steel.

A fixation mechanism is formed on the lead body 15 proximal to the electrode array 20 in the distal lead portion 50 that is adapted to be implanted in and engage subcutaneous tissue to inhibit axial movement of the lead body 15 and dislodgement of the stimulation electrodes 25, 30, 35 and 40. The fixation mechanism comprises four tine elements 125, 130, 135 and 140 arrayed in a tine element array 120 in the distal lead portion 50 of the lead body 15. As shown in FIGS. 1 and 2, the tine elements 125, 130, 135, and 140 are separate from the stimulation electrodes 25, 30, 35, and 40. In the example shown in FIGS. 1 and 2, the tine elements 125, 130, 135, and 140 are axially displaced from the stimulation electrodes 25, 30, 35, and 40.

Exemplary tine elements are depicted in FIGS. 2-4, where M=4 and N=4, for example. Each tine element 125, 130, 135 and 140 comprises at least one flexible, pliant, tine, and four such tines 145, 150, 155 and 160 or 145', 150', 155' and 160', are depicted in these examples. Each tine, e.g., tine 155 in FIG. 3 or 155' in FIG. 4, has a tine width and thickness and extends through a tine length from an attached tine end 165 to a free tine end 170. The attached tine end 165 is attached to the lead body 15 from a tine attachment site and supports the tine extending outwardly of the lead body 15 and proximally toward the lead proximal end 85. The tines are adapted to be folded inward against the lead body 15 when fitted into and constrained by the lumen of an introducer such that the tine free ends of more distal tines of more distal tine elements are urged toward or alongside the attached tine ends of the adjacent more proximal tines of more proximal tine elements, and the folded tines do not overlap one another.

In the depicted preferred embodiments, the tine elements 125, 130, 135 and 140 or 125', 130', 135' and 140' preferably comprise a tine mounting band 175 or 175' encircling the lead body with the tines extending from respective attached tine ends or roots disposed apart from one another, preferably at equal spacing, around the tine mounting band 175 or 175'. The four tines 145, 150, 155 and 160 or 145', 150', 155' and 160', have a tine thickness that enables folding of the tines against the lead body in the space between the tine mounting band and the adjoining proximal tine mounting band depicted in FIGS. 1 and 2.

The mounting band 175, 175' is preferably about 0.062 inches in outside diameter and about 0.076 inches long. Each tine is preferably about 0.013 inches thick, is preferably about 0.069 inches long, and is preferably about 0.035 inches wide and extends radially outward and proximally at about 45° to the axis of the lead body and the mounting band 175, 175'.

In accordance with the method of implantation of the present invention, the tines of the tine element array 120 along the length of the lead body 15 are folded proximally against the lead body 15 when the stimulation electrode array 20 and the tine element array 120 are inserted into the lumen of an introducer. Preferably, the stiffening stylet 100 is inserted through the lead body lumen to stiffen the lead 10 as it is advanced into and through the introducer lumen. Visual and radiographic imaging bands 90 and 95 are formed around the lead body 15 distal to and proximal to, respectively, the tine element array 120 to be employed in determining the location of the tine element array 120 within the introducer lumen and as the introducer is withdrawn to expose the tine element array 120. Visual and radiographic markers are optionally disposed along the introducer, and any guide wire used in implantation and the stylet to assist in pre-positioning the lead for implantation.

The folded tines attempt to resume their unrestrained angle as shown in FIGS. 1-4 away from the lead body when the lead is released from the distal lumen end opening of the introducer lumen. The tines resist being folded or inverted distally and present a folded cross-section profile that exceeds the lumen diameter inhibiting retraction proximally back through the distal lumen end opening of the introducer lumen. In one preferred embodiment, the tine elements 125, 130, 135 and 140 are formed of a bio-compatible plastic, e.g., medical grade silicone rubber or polyurethane, that can be formulated to exhibit a desired degree of stiffness or flexibility. In a further preferred embodiment, the tine elements 125, 130, 135 and 140 are formed of a superelastic alloy material.

FIGS. 5-8 depict the primary steps of implanting the sacral nerve stimulation lead 10 of FIGS. 1-4 and variations thereof described herein. An introducer 200 receives the distal segment 50 of the lead body 15 including the electrode array 20 and the tine element array 120 disposed within the introducer lumen. The stylet 100 is disposed within the lead body lumen so that its distal tip closes the lumen distal end opening. The assembly is advanced percutaneously at a selected angle until the introducer distal end is disposed at the selected foramen as shown in FIG. 5.

To determine the best location of the stimulation electrodes, an insulated needle with both ends exposed for electrical stimulation is used to locate the foramen and locate the sacral nerve by applying electrical stimulation through the needle using an external pulse generator. The efficacy of the location is tested by evaluating the physiologic response in relation to the electrical threshold energy required to elicit the response. For control of incontinence, the physician preferably implants the medical electrical lead 10 near the S3 sacral nerves. The implantable medical electrical lead 10 may, however, be inserted near any of the sacral nerves including the S1, S2, S3, or S4, sacral nerves accessed via the corresponding foramen depending on the necessary or desired physiologic response.

The advancement of the introducer 200 can be accomplished separately over a guide wire previously percutaneously advanced from the skin incision into the foramen to establish the angle of advancement. Also, a two-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately provides the introducer 200 in the location depicted in FIG. 5.

The lead 10, optionally stiffened by the stiffening stylet 100 disposed in the lead lumen, is advanced through the introducer lumen proximal end opening into the introducer lumen. However it is accomplished, the stimulation electrode array 20 and the tine element array 120 are disposed within the introducer lumen pre-positioned to be implanted in relation to the sacral nerve accessed through the foramen and in the subcutaneous tissue, respectively.

The stylet 100 may be advanced distally through the foramen as depicted in FIG. 5 or the neurostimulation lead 10 and the stylet wire 100 can both be advanced distally out of the introducer lumen distal end opening to advance the stimulation electrode array 20 into or through the foramen from the posterior entrance into casual contact with the more anterior sacral nerve as shown in FIG. 6.

The introducer 200 is retracted proximally after electrical testing to establish optimal positioning is completed, whereby the distal-to-proximal tine elements 125, 130, 135 and 140 or 125', 130', 135' and 140' are successively released from the introducer lumen distal end opening as shown in FIG. 7. The marker, 90, can be seen under fluoroscopy. This allows the physician to know that the tines are about to be deployed, as the marker 90 approaches the distal end of the fluoroscopically visible introducer sheath. When marker 95 passes the distal end of the sheath, all of the tines have been deployed. When the tines of each tine element are released in subcutaneous tissue, they bear against the tissue and inhibit proximal retraction of the lead body through the subcutaneous tissue if traction is applied to the lead body since the tines resist inversion in the proximal direction. The introducer 200 and lead stylet 100, if present, are completely removed in FIG. 7. As shown in FIG. 8, the proximal portion 55 of the lead body is bent laterally with respect to the distal portion 50 of the lead body 15 and implanted through a subcutaneously tunneled path to the neurostimulator IPG.

Alternative embodiments of the arrangement of the tines of the tine element array of the sacral nerve stimulation lead are depicted in FIG. 9. The N tine attachment points around the common circumference of a distal tine element are preferably offset radially from the N tine attachment points around the common circumference of the adjacent proximal tine element. In this embodiment, the tine lengths can be longer than the distance between the common circumferences of the proximal and distal tine elements along the lead body length because the N tines of each more distal tine element can be interleaved between the N tines of each more proximal tine element when constrained within an introducer lumen.

Exemplary tine elements are depicted in FIG. 9, where M=4 and N=4, for example, mounted on a lead body 15 of lead 10'. Thus, in FIG. 9, the tine elements 225, 230, 235, and 240 are formed as described above with respect to tine elements 125, 130, 135, and 140 or 125', 130', 135', and 140' as individual elements mounted in the tine element array 220 or integrally. The four tine attachment points around the common circumference of a distal tine element, e.g., tine element 240 are preferably offset radially by 45° from the N tine attachment points around the common circumference of the adjacent proximal tine element, e.g., tine element 235, so that the distal tines fold down interleaved between proximal tines when constrained within an introducer lumen.

Furthermore, alternate stimulation electrodes can be substituted for one or more of the P stimulation electrodes, and P can be equal to one. In FIG. 10, electrode 30' of lead 10" is preferably formed of a flexible elongated mesh or wire coil that can bend somewhat to fit through a foramen to locate the elongated electrode optimally with respect to a sacral nerve. The elongated electrode surface area of the flexible electrode 30' is preferably in the range of about 10.0 mm to about 38.0 mm and creates a wider electric field which allows the lead to be placed in a less precise or gross manner while still providing adequate electrical stimulation to the sacral nerve. The elongated flexible electrode 30' preferably comprises a wire coil and a band or ring-shaped electrode connector. The wire coil is formed of a platinum or platinum-iridium alloy wire having a diameter of about 0.1 mm wound over a mandrel. The outer diameter of the wire coil electrode 30' is preferably about the same as the outer diameter of the outer tubular sheath 15, the ring electrodes and connector elements and the insulator bands between the electrodes so that the lead 10 has a common outer diameter through its length.

Further variations of the disclosed preferred embodiments will occur to those of skill in the art. It is within the scope of the present invention to form the tine elements 125, 130, 135 and 140 or 125', 130', 135' and 140' and 225, 230, 235, and 240 as a single structure with a common tine mounting band extending the length of the tine element array 120 or as an integral section of the outer sheath of the lead body 15 extending through the length of the tine element array 120. Furthermore, whereas the depicted N tines are equal in number, it will is also within the scope of the invention to make the number N not equal among the M tine elements. For example, in one tine element, N=1, another tine element N=2, a further tine element N=4, etc. Moreover, whereas the M tine elements are depicted as equally spaced in the tine element array, the spacing can be varied. It may be desirable to include one or more tine element more proximally disposed along the lead body to be disposed proximally to the bend depicted in the lead body in FIG. 8 to aid in securing the lead or preventing dislodgement of the stimulation electrodes.

Accordingly, the present invention advantageously provides a unique implantable medical electrical stimulation lead that provides adequate stimulation of the sacral nerves for control of incontinence and other pelvic floor disorders with the sacral nerves and with less sensitivity to placement. The unique leads simplify the implantation procedure and reduce or eliminate the need to reprogram the stimulation energy level provided by the neurostimulator IPG or to re-position the stimulation electrodes.

The medical electrical leads and procedures of the present invention can be used to stimulate multiple nerves or multiple sides of a single nerve bundle. In addition, the medical electrical lead 10 can also be used as an intramuscular lead where the tines can engage against muscle and assist in preventing dislodgement of the distal electrode(s). This may be useful in muscle stimulation such as dynamic gracilloplasty or stomach stimulation for gastroparesis or obesity.

All patents and publications referenced herein are incorporated herein by reference in their entireties.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

The invention claimed is:

1. A system comprising:
an implantable medical lead comprising:
a lead body extending between a proximal end and a distal end;
a plurality of conductors within the lead body;
a plurality of electrodes, wherein each electrode is electrically connected to a conductor of the plurality of conductors; and
a plurality of tine elements extending from the lead body, wherein all tine elements of the plurality of tine elements are positioned between a most proximal electrode of the plurality of electrodes and the proximal end of the lead body, each tine element comprising a plurality of flexible, pliant tines, each tine having a tine width and thickness and extending a tine length from an attached tine end to a free tine end, the attached tine end attached to the lead body from a tine attachment site and supporting the tine extending outwardly of the lead body and proximally toward the lead proximal end, wherein the plurality of tines of the plurality of tine elements are adapted to be folded inward against the lead body when fitted into and constrained by a lumen of an introducer without overlapping one another and deploy outward to engage body tissue when the introducer is withdrawn to release the plurality of tines, wherein the plurality of tine elements is separate from and axially displaced from the plurality of electrodes.

2. The system of claim 1, wherein the tines of the tine elements are formed of a flexible, bio-compatible plastic selected from the group consisting of medical grade polyurethane compounds and silicone rubber compounds.

3. The system of claim 1, wherein the tines of the tine elements are formed of a flexible, implantable grade super-elastic alloy.

4. The system of claim 1, wherein the tine attachment sites of the plurality of tine elements are separated longitudinally along the lead body by a distance that is greater than or equal to the tine length so that the tines are not overlapping one another when the tines are folded against the lead body towards the proximal end of the lead body.

5. The system of claim 1, wherein tine lengths and tine widths of tines of a first tine element of the plurality of tine elements are configured to enable the tines of the first tine element to fold toward the proximal end of the lead body alongside and interleaved with tines of a second tine element of the plurality of tine elements, the second tine element being located closer to the proximal end of the lead body than the first tine element.

6. The system of claim 1, wherein a number of tine elements in the plurality of tine elements is equal to a number of tines in the plurality of tines of each tine element.

7. The system of claim 1, wherein each tine element in the plurality of tine elements comprises an equal number of tines.

8. The system of claim 1, wherein at least one of the electrodes of the plurality of electrodes comprises an elongated, flexible electrode configured to assume a curve when implanted in relation to body tissue.

9. The system of claim 1, wherein the tine attachment sites of each tine element of the plurality of tine elements are disposed in a common circumference of the lead body, and the tine attachment sites of adjoining tine elements along the lead body are radially offset from one another around the common circumference such that the tine free ends of the tines of each adjacent tine element are configured to engage against body tissue at radially and axially separated points along the lead body.

10. The system of claim 1, further comprising the introducer.

11. A system comprising:
an implantable pulse generator configured to generate electrical stimulation; and
an implantable medical lead configured to be electrically coupled to the implantable pulse generator and introduced through and released into body tissue via an introducer defining an introducer lumen, the implantable medical lead comprising:
a lead body extending between a proximal end and a distal end;
a plurality of conductors within the lead body;
a plurality of electrodes, wherein each electrode is electrically connected to a conductor of the plurality of conductors; and a plurality of tine elements extending from the lead body, wherein all tine elements of the plurality of tine elements are positioned between a most proximal electrode of the plurality of electrodes and the proximal end of the lead body, each tine element comprising a plurality of flexible, pliant tines, each tine having a tine width and thickness and extending a tine length from an attached tine end to a free tine end, the attached tine end attached to the lead body from a tine attachment site and supporting the tine extending outwardly of the lead body and proximally toward the lead proximal end, wherein the plurality of tines of the plurality of tine elements are adapted to be folded inward against the lead body when fitted into and constrained by the lumen of the introducer without overlapping one another and deploy outward to engage body tissue when the introducer is withdrawn proximally, wherein the plurality of tine elements is separate from and axially displaced from the plurality of electrodes.

12. The system of claim 11, wherein the tines of the tine elements are formed of a flexible, bio-compatible plastic selected from the group consisting of medical grade polyurethane compounds and silicone rubber compounds.

13. The system of claim 11, wherein the tines of the tine elements are formed of a flexible, implantable grade superelastic alloy.

14. The system of claim 11, wherein the tine attachment sites of the plurality of tine elements are separated longitudinally along the lead body by a distance that is greater than or equal to the tine length so that the tines are not overlapping one another when the tines are folded against the lead body towards the proximal end of the lead body.

15. The system of claim 11, wherein tine lengths and tine widths of tines of a first tine element of the plurality of tine elements are configured to enable the tines of the first tine element to fold toward the proximal end of the lead body alongside and interleaved with tines of a second tine element of the plurality of tine elements, the second tine element being located closer to the proximal end of the lead body than the first tine element.

16. The system of claim 11, wherein at least one of the electrodes of the plurality of electrodes comprises an elongated, flexible electrode configured to assume a curve when implanted in relation to body tissue.

17. The system of claim 11, wherein the tine attachment sites of each tine element of the plurality of tine elements are disposed in a common circumference of the lead body, and the tine attachment sites of adjoining tine elements along the lead body are radially offset from one another around the common circumference such that the tine free ends of the tines of each adjacent tine element are configured to engage against body tissue at radially and axially separated points along the lead body.

18. A method comprising:
 introducing an introducer into body tissue, the introducer defining a lumen extending between a lumen proximal end and a lumen distal end;
 advancing a medical lead through the lumen of the introducer, the medical lead comprising:
  a lead body extending between a proximal end and a distal end;
  a plurality of conductors within the lead body;
  a plurality of electrodes, wherein each electrode is electrically connected to a conductor of the plurality of conductors; and
  a plurality of tine elements extending from the lead body, wherein all tine elements of the plurality of tine elements are positioned between a most proximal electrode of the plurality of electrodes and the proximal end of the lead body, each tine element comprising a plurality of flexible, pliant tines, each tine having a tine width and thickness and extending through a tine length from an attached tine end to a free tine end, the attached tine end attached to the lead body from a tine attachment site and supporting the tine extending outwardly of the lead body and proximally toward the lead proximal end, wherein the plurality of tines of the plurality of tine elements are adapted to be folded inward against the lead body when fitted into and constrained by the lumen of the introducer without overlapping one another and deploy outward to engage body tissue when the introducer is withdrawn proximally, wherein the plurality of tine elements is separate from and axially displaced from the plurality of electrodes; and
 withdrawing the introducer from the body tissue to deploy the plurality of tine elements.

19. The method of claim 18, wherein introducing the introducer into body tissue comprises percutaneously introducing the introducer through body tissue.

20. The method of claim 18, wherein withdrawing the introducer from the body tissue to deploy the plurality of tine elements comprises withdrawing the introducer from the body tissue to deploy the plurality of tine elements into subcutaneous tissue, wherein the plurality of tine elements engage with the subcutaneous tissue to inhibit axial movement of the lead body and dislodgement of the plurality of electrodes.

21. The method of claim 18, wherein withdrawing the introducer from the body tissue to deploy the plurality of tine elements comprises anchoring, with the plurality of tine elements, the plurality of electrodes in operative relation to a selected stimulation site.

22. The system of claim 1, further comprising a tine mounting band, wherein at least one tine element is mounted to the lead via the tine mounting band.

23. The system of claim 11, further comprising a tine mounting band, wherein at least one tine element is mounted to the lead via the tine mounting band.

24. The method of claim 18, wherein the medical lead further comprises a tine mounting band, wherein at least one tine element is mounted to the lead via the tine mounting band.

* * * * *